United States Patent [19]

Doyle

[11] 4,129,781
[45] Dec. 12, 1978

[54] FILM THICKNESS MEASURING APPARATUS AND METHOD

[76] Inventor: Walter M. Doyle, 2875 Bernard Ct., Laguna Beach, Calif. 92651

[21] Appl. No.: 687,240

[22] Filed: May 17, 1976

[51] Int. Cl.² ............................................. G01J 1/00
[52] U.S. Cl. .................................... 250/341; 250/338
[58] Field of Search ............... 250/338, 340, 339, 341; 356/114, 118, 119

[56] References Cited

U.S. PATENT DOCUMENTS

| | | | |
|---|---|---|---|
| 3,355,980 | 12/1967 | Mathias | 356/118 |
| 3,426,201 | 2/1969 | Hilton et al. | 250/339 X |
| 3,437,811 | 4/1969 | Willis et al. | 250/339 X |
| 3,824,017 | 7/1974 | Galyon | 356/118 X |
| 3,904,293 | 9/1975 | Gee | 356/118 |
| 3,994,586 | 11/1976 | Sharkins et al. | 250/341 X |
| 4,015,127 | 3/1977 | Sharkins | 250/341 |

Primary Examiner—Davis L. Willis
Attorney, Agent, or Firm—Thomas J. Plante

[57] ABSTRACT

An optical apparatus is disclosed for measuring and monitoring the thickness of a partially transparent film, or coating, which is either self-supporting or attached to a reflecting substrate. Infra-red radiation strikes the reflecting surface at an angle of incidence which is at or near the Brewster's angle of the film material. The radiation is polarized in its plane of incidence, which must be maintained substantially parallel to any stria in the reflecting surface. The polarization may be provided by germanium plates which receive the radiation at an angle of incidence at or near the Brewster's angle of the germanium.

7 Claims, 4 Drawing Figures

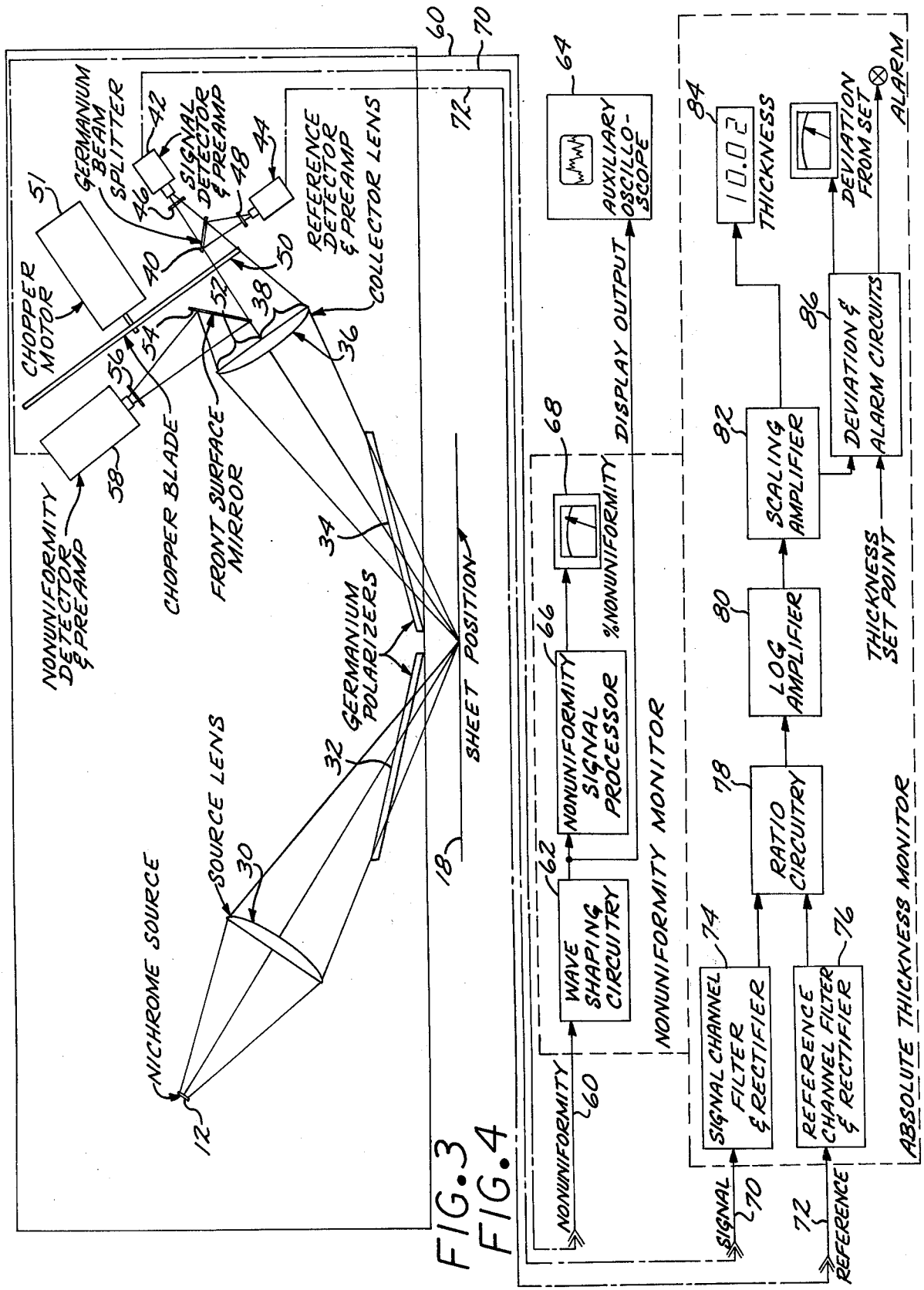

FILM THICKNESS MEASURING APPARATUS AND METHOD

BACKGROUND OF THE INVENTION

This invention relates to optical apparatus for measuring the thickness or chemical composition of partially transparent films, which are either self-supporting or attached to a reflecting substrate. Such equipment is useful in laboratory settings, and is also highly valuable for process control functions. It is particularly desired to provide an industrial coating monitor which will function on-line during the manufacturing process to measure continuously the thickness of plastic coatings on metal surfaces.

Infra-red absorption techniques have long been used to identify and analyze a wide variety of materials. In particular, techniques have been developed for determining the thickness and composition of film by measuring and comparing the transmission of radiation at two or more wavelengths. (Miller and Mounsey Paper regarding "On-Line Measurement Of Blown & Cast Film-Profile and Average Gauge Utilizing Infrared Techniques" in 1971 TAPPI Plastics-Paper Conference). Most commonly, these techniques involve a source of infrared radiation on one side of the film and a detector on the other.

There are many measurement situations in which it is either not convenient or not possible to place the source and receiver on opposite sides of the film. One example would be an organic polymer coating on an opaque substrate such as paper or metal. In such cases, it is necessary to place the detector on the same side of the target as the source and analyze the radiation which is transmitted through the coating and reflected back by the substrate. In the past, the operation of such reflective film gauges has been limited by the fact that the front surface of the coating reflects several percent of the radiation which strikes it. The radiation reflected by this first surface interferes with the radiation transmitted through the film and reflected by the substrate, in such a way as to give rise to a variation in the measured signal. This is dependent on the optical phase shift in the film and hence on both the film thickness and the wavelength of the radiation.

Designs have previously been proposed to minimize the problem of first surface reflection. For diffuse substrates such as paper, a fairly simple design has been found to be adequate (Brunton U.S. Pat. No. 3,693,025). In this case, the substrate surface is rough, whereas that of the coating is relatively smooth. As a result, the substrate reflects diffusely, i.e., in all directions; whereas the surface reflection is specular, i.e., confined to a narrow range of directions. The first surface reflection can be avoided by placing the radiation source and the detector subsystem at positions so that the optical rays between them and the surface make different angles with the normal to the surface. The specular reflection from the first surface will then miss the detector, but enough of the diffuse second surface reflection will be received to allow system operation.

Techniques have also previously been proposed for reducing the first surface effects in the case of coatings on specular substrates (Brunton U.S. Pat. No. 3,631,526). In this case, both the first and second surface reflections are specular and thus cannot be distinguished on the basis of their directionality. The three approaches proposed amount to: (1) averaging over a range of incidence angles; (2) using adjacent wavelengths; and (3) averaging over a range of wavelengths. All three of these approaches have been found experimentally to yield too little improvement to be useful for many applications of interest. The following items include all other prior art known to applicant: Brun Infra-Gauge BF-100 Brochure; Brunton U.S. Pat. Nos. 3,597,616; Brunton et al 3,790,796; and Van Horne et al 3,803,414.

SUMMARY OF THE INVENTION

The present invention solves the problem of first surface reflection by providing a measurement geometry which reduces the intensity of this reflection to a negligible level. The invention includes at least three significant concepts, which are considered to be individually, as well as collectively, important advances in this field:

(1) the use of an angle of incidence and reflection for which one state of optical polarization is not reflected, (2) the use of a plane of incidence and reflection which eliminates the harmful effects of the surface stria brought about by the large incidence angle necessitated by the first concept, and (3) the provision of a practical means for restricting the radiation to the required polarization state.

The first concept involves the use of a plane polarized radiation incident at the coating's Brewster angle. The second concept involves the use of a plane of incidence parallel to the stria in the surface being coated, in order to obviate the effects of diffraction by the stria. And the third concept involves the use of high index flat plates to achieve a sufficient approximation to plane polarization.

BRIEF DESCRIPTION OF THE DRAWINGS

FIG. 3 is a schematic showing of the optical portion of a preferred embodiment of a complete optical film-measuring system incorporating the present invention; and FIG. 4 is a block diagram illustrating the electronic portion of the system shown in FIG. 3.

DETAILED DESCRIPTION OF PREFERRED EMBODIMENT

Figure 1:
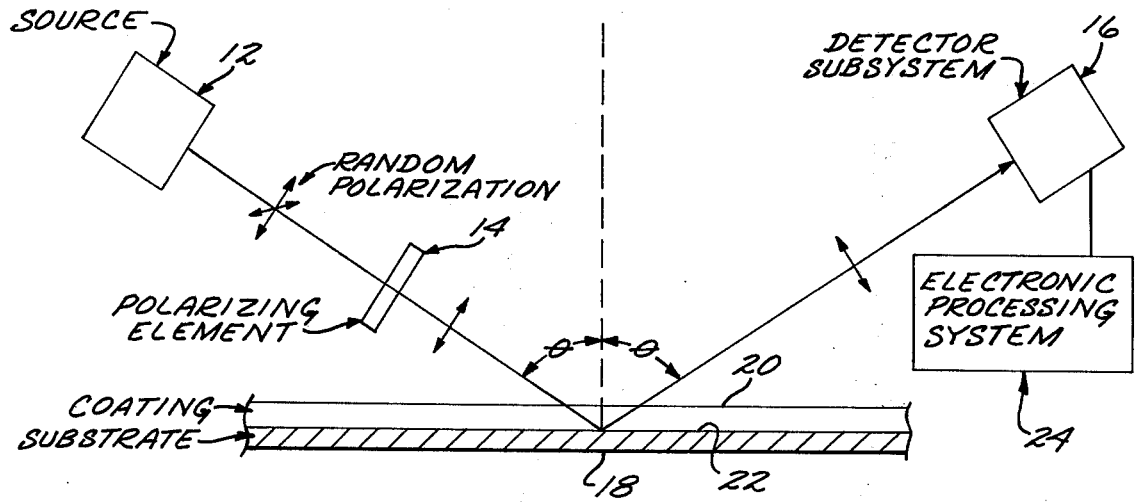
FIG. 1 is a schematic illustration of an infra-red coating monitor embodying the broad concepts involved in the invention.

In FIG. 1, the source 12 of infra-red radiation will normally emit randomly polarized radiation. In other words, its electric field will not have a well defined direction. The polarizing element 14 is used to eliminate those components of the electric field which are perpendicular to the plane of incidence. The plane of incidence is the plane formed by the source 12, the detector 16, and the point of incidence 18 of the light on the coated surface. This polarization by element 14 leaves the radiation plane polarized with its polarization in the plane of incidence.

The angle of incidence, $\theta$, is set equal to Brewster's angle of the coating, which means that $\theta = \tan^{-1} n$, where $n$ is the index of refraction of the coating (typically 1.6). At this angle, radiation polarized in the plane of incidence will not be reflected by the coating surface 20. As a result, the radiation reaching the detector is obtained solely by reflection at the coating-substrate interface 22.

The detector 16 constitutes a subsystem which may include one or more infra-red detectors combined with appropriate wavelength selecting filters and connected to an electronic system 24 designed to analyze the signals obtained to provide a readout of coating thickness or other desired quantities.

Figure 2:
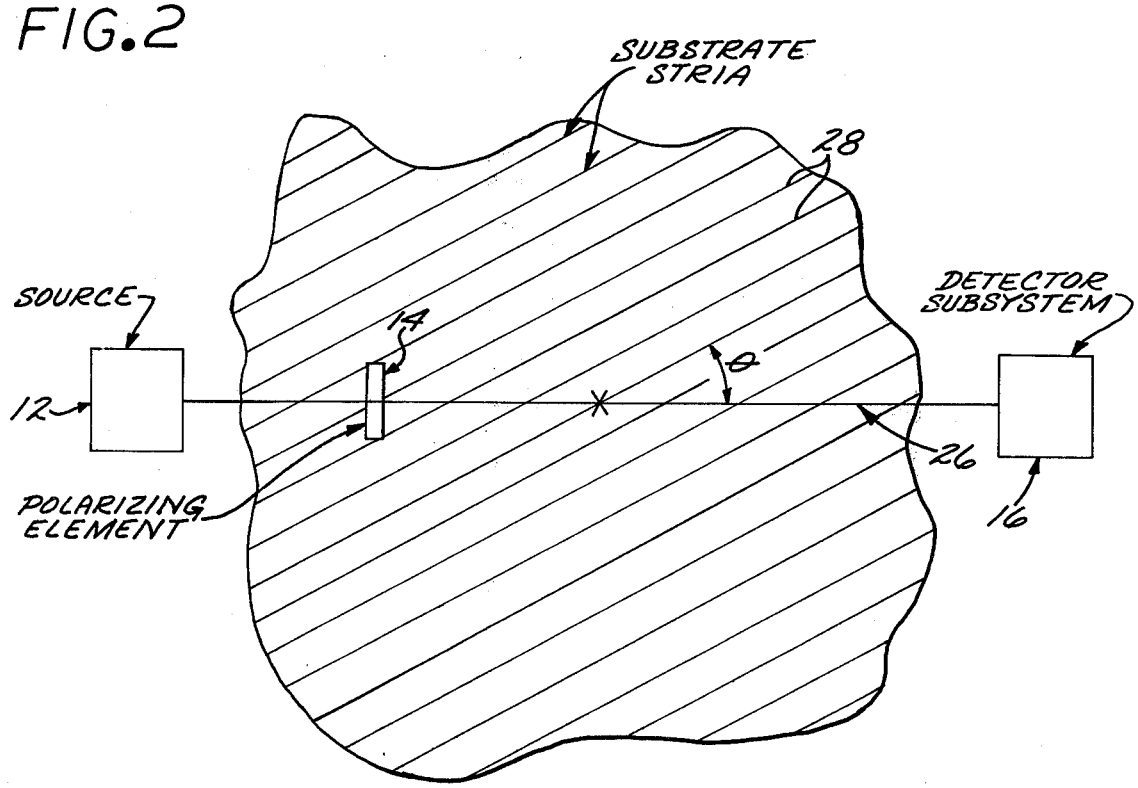
FIG. 2 is a schematic illustration used to explain the requirement that the coating monitor be oriented in a specific direction relative to the stria of the monitored surface, in order to function properly.

The geometry illustrated by FIG. 1 is not sufficient to insure proper operation of the film gauge for most common substrates. The reason for this is that many substrates are produced by rolling processes which result in fine grooves (or stria) parallel to the rolling direction. As will be explained in more detail later, these stria act as a diffraction grating, giving rise to a wavelength-dependent deflection of the reflected radiation away from the ideal specular direction. This effect introduces substantial measurement errors unless the plane of incidence is made parallel to the stria direction. Referring to the top view of the measurement geometry, FIG. 2, the necessary condition corresponds to the orientation wherein the angle $\theta=0$, $\theta$ being the angle between the plane of radiation incidence 26 and the direction of the stria 28.

A more complete embodiment of the subject invention is illustrated in FIG. 3. The source 12 is an electrically heated nichrome strip which provides infra-red radiation. This radiation is collected by a lens 30 and imaged at the surface 18 of the coated sheet. Because of the need to collect sufficient power, the optical rays striking the surface span a range of incidence directions. However, the source and lens position are chosen so that the incidence angles approximate Brewster's angle for the coating. For a coating index of 1.6, Brewster's angle is 58°, measured from the normal to the surface.

High quality infra-red polarizers are quite expensive. In order to make this invention economically practical, I use flat sheets 32 and 34 of optical material which serve as partial polarizers if the radiation passes through them at or near the appropriate Brewster's angle for their refractive index. This method is used in the instrument shown in FIG. 3 to achieve an approximation to plane polarization. A high index material such as germanium (n=4) is used so that a sufficient degree of polarization can be obtained with a minimum number of elements.

Further, only one-half of the radiation distribution is used for accurate measurement so that Brewster's angle can be most nearly approximated for this half. Specifically the lower half of the distribution is used for accurate thickness measurement, whereas the upper half is used for less accurate but rapid measurement. For germanium, Brewster's angle is approximately 76°. Radiation striking the germanium flats at this angle will be almost 90% polarized in the plane of incidence after passing through the two flats (4 surfaces) shown. Note that the performance would be unchanged if both flats were placed in either the transmitting or receiving leg of the gauge, but that the symmetrical design shown is convenient in that it minimizes their required size.

The radiation reflected by the surface 18 of the coated sheet is collected by lens 36. The lower half 38 of this lens directs received radiation to the beamsplitter 40, which divides the radiation between the signal channel detector 42 and the reference channel detector 44. Interference filters 46 and 48 select the appropriate parts of the infra-red spectrum to provide the needed coating thickness information. The signal filter 46 selects a spectral band for which the coating is absorbing, whereas the reference filter 48 selects a band for which it is relatively transparent. The ratio of the two signals can then be electrically processed in such a way as to yield a measurement of coating thickness. The chopper 50, driven by motor 51, interrupts the signal so as to give a repetitive zero signal reference for sensitive absolute measurement.

The radiation striking the upper half 52 of the receiver lens is directed by mirror 54 to filter 56 and detector 58. This channel is designed for rapid, but less accurate, nonuniformity monitoring. The processing electronic systems for both the absolute thickness and the nonuniformity functions are illustrated in FIG. 4.

As shown in FIG. 4, the electrical signal output of detector 58, which has converted the received radiation to an electrical signal, is fed via conductor 60 to wave shaping circuitry 62. The output of the detector 58 is an electrical signal dependent on the fluctuations in the optical field. The wave shaping circuitry processes this electrical signal in such a way as to produce an output proportional to the instantaneous optical power.

The output from the wave shaping circuitry can be fed directly to an oscilloscope 64 to visually display coating non-uniformities. Also, the output from the wave shaping circuitry is rectified by the nonuniformity signal processor 66 to yield a visual meter reading of nonuniformity percent at the meter 68.

The electrical signals obtained from signal detector 42 and reference detector 44 are fed, via conductors 70 and 72, respectively, to the filter and rectifier circuits 74 and 76, respectively. The rectifiers are synchronized with chopper 50. Their outputs are proportional to the average optical intensity of the chopped radiation.

The ratio circuitry 78, which receives the output signals from both rectifiers 74 and 76, serves to cancel out effects common to the signal and reference channels. The log amplifier 80 linearizes the output, providing a signal proportional to coating thickness. A scaling amplifier 82 establishes the calibration and drives a panel meter 84, giving a thickness indication in milligrams per square inch, or other desired units. Optional deviation and alarm circuits 86 may be provided for user convenience.

The discussion so far has been devoted primarily to applications in which the film under study is attached to a reflecting substrate. However, the general techniques described are also of use for measuring self supporting film. The embodiment already described can be used for such applications by adding a reflector behind the film to take the place of the substrate. In addition, the plane-polarized, Brewster's angle approach can be used with the source and detector subsystem on opposite sides of the film. Furthermore, diffraction effects due to film thickness stria may still require an incidence plane parallel to the stria.

THEORETICAL DISCUSSION

The reflectance of a dielectric surface at normal incidence is $r=(n-1)^2/(n+1)^2$. For a coating having $n=1.6$, this is 0.053. At first thought it might seem that a 5% reflection is not especially significant. However, if we are using absorption to determine the properties of a film, it is quite possible that the amplitude of the radiation transmitted by the film and reflected by the substrate will be attenuated to the point where it is comparable to the amplitude of the first surface reflection. When these two signals are superimposed on leaving the surface, they will either tend to reinforce or to cancel each other, depending on the phase relationship between them. For example, if both signals happen to have intensities equal to 5% of the incident level, the combined signal can vary from 0 to almost 20% depending on phase. The maximum reflectance will be obtained whenever $\lambda = 2nd \cos \theta'/(m-\frac{1}{2})$, where $\lambda$ is the wavelength, n is the index of refraction, d is the film thickness, $\theta$ is the angle of propagation in the film, and m is any integer. Thus, the measured signal can vary quite markedly as a function of wavelength, and of coating thickness.

The effect described above is sufficiently severe to greatly reduce the utility of a film gauge operating at normal incidence. My early attempts to overcome this problem involved using a wide optical acceptance angle so as to average the effect over a range of $\theta$ values. These attempts were not successful.

When light enters a dielectric material it is refracted (deflected) toward the normal to the surface. The relationship between the angle of incidence, $\theta$, and that of refraction, $\theta'$, is given by Snell's law: $\sin \theta / \sin \theta' = n$, where n is the index of refraction of the dielectric. In general, the amplitudes of the refracted and reflected beams of light depend on n, on $\theta$, and on the polarization state of the light. Brewster discovered the law that if the refracted and reflected beams make an angle of 90° with each other no light will be reflected which is plane polarized in the plane of incidence. This condition can be shown to correspond to $\tan \theta = n$, where this value of $\theta$ is known as Brewster's angle. My invention minimizes the effects of interference by using a propogation direction which approximates this angle.

Operation at Brewster's angle, or any angle other than normal incidence, introduces a new problem, which can severely limit instrument performance if not handled properly. This problem is diffraction by surface stria.

Diffraction is a fundamental result of the wave nature of light. Its most simple form is an angular spreading of a beam of light which occurs most simple form is an angular spreading of a beam of light which occurs whenever the light is interrupted by an obstacle, whether it be the edge of an obstruction, a small opening, or a scratch on a reflector. If the obstacle happens to be periodic, such as an array of slits or a pattern of scratches, the diffraction phenomenon will be organized into an angular pattern which may have periodic features. This effect is the basis of the diffraction grating, a device which is formed by scribing fine lines on a reflecting surface.

Collimated single wavelength radiation, reflected by a diffraction grating, will diffract into several directions with the angular positions of the intensity maxima being given by the grating equation: $d (\sin \theta_i - \sin \theta_d) = m\lambda$. Here d is the spacing between the grooves, $\theta_i$ and $\theta_d$ are angles of incidence and defraction, $\lambda$ is the wavelength, and m is any integer, including zero. It should be noted that $\theta_i$ and $\theta_d$ are normally assumed to lie in a plane perpendicular to the grooves. By reviewing the derivation of the grating equation, it can be shown that, if the actual incidence and viewing directions are not in this plane, their projections on the plane should be used in the equation.

The typical striated substrate material is, in effect, a poor quality diffraction grating. For non-zero values of $\theta_i$ and $\theta_d$, the received intensity will depend highly on wavelength, inasmuch as the angular position of the detector subsystem will correspond to a maximum for some wavelengths and a minimum for others. This is especially troublesome in apparatus of the type disclosed herein, in that my instrument functions by comparing intensities at different wavelengths to determine film characteristics.

The problem vanishes for normal incidence. In this case, $\theta_i = \theta_d = 0$ and the grating equation predicts a maximum for all wavelengths when $m = 0$, and no maxima when m is not zero. Thus, the grating effect may lead to a reduction in signal level, but it will not give rise to a wavelength dependence under this condition.

The same result will hold true for non-normal incidence as long as the plane of incidence is made parallel to the stria. In this case, the incidence and viewing angles will not have projections in the plane perpendicular to the stria, and thus again $\theta_i = \theta_d = 0$. This condition is the only one in which a film gauge using a large angle of incidence will function properly for striated substrates.

SUMMARY

In recapitulation, attention is called to the solutions of the problems discussed above under the Summary of the Invention. The problem of signal interference resulting from surface reflection of the coating, or film, is solved by having an angle of radiation incidence which is at or near the Brewster's angle of the coating material and a direction of polarization which is in the plane of incidence. This solution of one problem creates a diffraction problems because of the large incidence angle required, which problem I have solved by so orienting the plane of radiation incidence that it is parallel to the stria in the substrate. And, finally, the inherent problem of excessive cost created by the need to polarize the radiation in its plane of incidence has been solved by the use of one or more optical plates which receive the radiation at the Brewster's angle of their material. An additional benefit is provided by the division of the reflected radiation into a fast-action non-uniformity indication system and a highly accurate coating thickness measurement system.

The following claims are intended not only to cover the specific embodiment disclosed, but also to cover the inventive concepts explained herein, both singly and collectively, with the maximum breadth and comprehensiveness permitted by the prior art.

What I claim is:

1. An apparatus for measuring the thickness of a film on a reflecting surface wherein the measurement is optically accomplished by light radiation propagating in a plane of incidence which is substantially parallel to the stria in the reflecting surface.

2. A film-thickness measuring apparatus comprising:
   a light detection and comparison subsystem;
   a light source which radiates light toward the film and its substrate at approximately the Brewster's angle of the film; and
   means for substantially polarizing the light radiation to the plane of incidence of the light on the film and its substrate;
   the plane of incidence of the light radiation being substantially parallel to the stria in the substrate of the film.

3. The apparatus of claim 2 wherein the polarizing means comprises one or more flat sheets of optical material which receive the light radiation at approximately their own Brewster's angle of light incidence.

4. The apparatus of claim 3 wherein the light detection means comprises:
first light-responsive means which respond to a band of wavelengths which is significantly absorbed by the film;
second light responsive means which respond to a band of wavelengths which is not significantly absorbed by the film; and
means for ratioing the responses of the first and second light-responsive means to produce a signal which is dependent on light absorption but which is relatively insensitive to optical effects common to both bands of wavelengths.

5. The apparatus of claim 2 wherein the light detection means comprises:
first light-responsive means which respond to a band of wavelengths which is significantly absorbed by the film;
second light responsive means which respond to a band of wavelengths which is not significantly absorbed by the film; and
means for ratioing the responses of the first and second light-responsive means to produce a signal which is dependent on light absorption but which is relatively insensitive to optical effects common to both bands of wavelengths.

6. Apparatus for continuously measuring the thickness of coating on a substrate comprising:
means for emitting infra-red radiation;
optical means for focusing the radiation on the substrate surface at approximately that angle of incidence which equals $tan^{-1}n$, where n is the index of refraction of the coating;
polarizing means for polarizing the radiation in the plane of incidence, said polarizing means comprising a germanium plate which is so oriented that the radiation entering it is at or near an angle which equals $tan^{-1}n$, where n is the index of refraction of the germanium plate;
the plane of incidence of the radiation being substantially parallel to the stria in the substrate; and
optical means for measuring the thickness of the coating, using the radiation distribution of the light reflected from the substrate.

7. That method of measuring the thickness of a film on a reflecting surface which comprises the following steps:
beaming infrared radiation at the film so oriented as to strike its surface at approximately the angle of incidence which is the Brewster's angle of the film, thereby minimizing reflectance from the film surface;
polarizing the radiation in its plane of incidence, the plane of incidence being so oriented as to be parallel to the stria in the reflecting surface;
optically detecting the amount of polarized radiation transmitted by the film and reflected from the reflecting substrate, producing therefrom an electrical signal which is dependent on absorption of radiation by the film; and
electrically converting such signal into a measurement of the thickness of the film.

* * * * *